United States Patent

Alneri et al.

[11] 4,113,973
[45] Sep. 12, 1978

[54] PROCESS FOR THE PREPARATION OF ANHYDROUS SOLUTIONS OF ALKALINE PHENATES IN ORGANIC SOLVENTS

[75] Inventors: Enzo Alneri; Giorgio Bottaccio; Stefano Campolmi; Luigi Cassar, all of Novara, Italy

[73] Assignee: Montedison S.p.A., Milan, Italy

[21] Appl. No.: 816,919

[22] Filed: Jul. 19, 1977

[30] Foreign Application Priority Data

Jul. 23, 1976 [IT] Italy .................................. 25636/76

[51] Int. Cl.$^2$ .............................................. C07C 39/04
[52] U.S. Cl. ...................................... 568/716; 568/780
[58] Field of Search ........... 260/621 P, 624 R, 624 A, 260/621 R, 621

[56] References Cited

U.S. PATENT DOCUMENTS

| | | | |
|---|---|---|---|
| 2,579,329 | 12/1951 | Martin | 260/621 P |
| 2,807,643 | 8/1957 | Hortley | 260/520 |
| 3,062,897 | 11/1962 | Prutton et al. | 260/624 |

Primary Examiner—James O. Thomas, Jr.
Assistant Examiner—Werren B. Lone
Attorney, Agent, or Firm—Stevens, Davis, Miller & Mosher

[57] ABSTRACT

A process is disclosed for the preparation of anhydrous solutions of alkaline phenates in organic solvents, comprising the steps:
(a) synthesis in water of alkaline phenates by the reaction of sodium sulphate or potassium sulphate with calcium hydroxide and a phenol of the general formula:

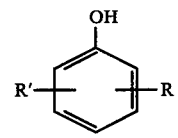

wherein R and R', which may be the same or different from each other, are hydrogen atoms or linear alkyl groups having up to 4 carbon atoms, at a temperature substantially lower than 30° C;
(b) filtering the calcium sulphate;
(c) quantitatively decalcifying the residual aqueous solution by the addition of an aqueous solution of NaOH or KOH, until a total concentration is reached which is at least equal to about 30% by weight of the total solution;
(d) filtering the precipitated calcium hydroxide and alkaline sulphate;
(e) extracting in countercurrent, at a temperature between 50° and about 90° C, the residual aqueous solution with at least one aprotic polar organic solvent; and
(f) dehydrating the organic solution of the alkaline phenates.

For the extraction in countercurrent of the aqueous residual solution, preferred organic solvents include β-picoline, dimethylether of diethylene glycol, quinoline, tetrahydrofuran, dimethylsulphoxide, sulpholane and N-methyl-morpholine. If desired, a non-polar diluent (e.g., toluene) may also be present.

6 Claims, No Drawings

PROCESS FOR THE PREPARATION OF ANHYDROUS SOLUTIONS OF ALKALINE PHENATES IN ORGANIC SOLVENTS

The present invention relates to a process for the preparation of anhydrous solutions of alkaline phenates in organic solutions. More particularly, the present invention relates to the preparation of organic solutions consisting or consisting essentially of phenates, of sodium or potassium, in particular polar aprotic solvents that are stable in an alkaline medium, miscible or immiscible with water, and in which solvents the phenates are soluble.

Still more specifically, the present invention resides in a polyphase cycle, at the end of which there are obtained anhydrous solutions of sodium phenates or potassium phenates in polar aprotic solvents, usable as such. The process may be integrated into any appropriate industrial cycle in which solutions of the kind described are useful.

The organic solutions of alkaline phenates thus obtained show in fact important applicational possibilities which make them particularly interesting from the industrial point of view.

In the field of organic syntheses in general, for instance, basic systems consisting or consisting essentially of a couple "alkaline phenate/polar aprotic solvent" find a useful application in many reactions in the mechanism of which there intervenes or occurs an extraction of protons from an activated reactant, which may be defined for convenience and brevity as a "substrate", into which functional groups are subsequently introduced.

For instance, solutions of the type which are one of the objects of this invention may be used in Kolbe reactions or in the carboxylation reaction with $CO_2$ of organic substrates containing activated hydrogen atoms.

Just for illustrative purposes and for more precisely defining one field of application of this invention, one may refer for instance to a conventional process for the synthesis of citric acid. Such conventional process comprises in a first stage the bicarboxylation reaction of acetone with $CO_2$ in a substantially anhydrous inert polar aprotic medium, such as the N-dialkyl-substituted amides of organic acids (in particular dimethylformamide), N-alkyllactams, dimethylsulphoxide, pyridine, picolines, quinoline, etc., in the presence of an alkaline phenate (Na, K), at a temperature between 0° and 80° C and under substantially atmospheric pressure.

While the alkaline phenate is converted into phenol, one obtains in this way the alkaline salt of the 3-keto-glutaric acid which is then separated.

The alkaline salt of the 3-keto-glutaric acid in aqueous solution is converted in the second stage to the corresponding cyanhydrin by reaction with HCN.

Then follows the saponification of the cyanhydrin with $H_2SO_4$, and the citric acid thereby obtained is then recovered by selective precipitation as an alkaline earth metal salt, or by extraction with solvents.

At the end of the above-described cycle given for purely illustrative and exemplifying purposes, and to better define the applicative aspects of the present invention, in consequence of the hydrolysis conducted with $H_2SO_4$, one disposes of residual waters essentially consisting of $Na_2SO_4$ or $K_2SO_4$ solutions, depending on the alkali present in the starting phenate, which are not re-cyclable as such and which therefore represent a considerable economical-environmental burden.

There thus arises the problem of their utilization, or at least of the recovery of the alkali present therein.

On the other hand, as stated above, in the reaction of this type, the alkaline phenate at the end is found as phenol which is separated, reconverted to phenate by means of alkali, and recycled.

The process which is an object of this invention, for instance, has its technical place and application potential in the solution of the problem of the recovery of alkali from the above-mentioned aqueous solutions by reconstituting the alkaline phenate in the aprotic polar solvents necessary for the process; in this instance for obtaining citric acid.

The preparation, according to this invention, of the anhydrous solutions of alkaline phenates in aprotic polar solvents may be described schematically as (a) the synthesis in an aqueous medium of alkaline phenates fron the corresponding alkaline sulphates, phenols and calcium hydroxide;

(b) the complete de-calcification of the aqueous alkaline phenate solutions thus obtained by the addition of a concentrated alkali solution; and (c) the extraction with the desired polar aprotic organic solvent of the aqueous solution obtained in (b).

No previous processes systematically directed towards the preparation of the solutions of alkaline phenates which are the object of this invention are known.

Known technologies that have been described, but that have only a partial relevance but not with respect to the process of the invention as a whole, are the following:

Known per se is the double exchange reaction:

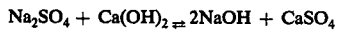

$$Na_2SO_4 + Ca(OH)_2 \rightleftarrows 2NaOH + CaSO_4 \qquad [1]$$

yet the described yields in NaOH do not exceed 50–60% with low concentrations (from 2.7 to 7 g/lt.) retrogradable upon evaporation, wherefore the possibilites for its industrial use are practically negligible.

On the other hand, also per se known, for instance for the elimination of $CaSO_4$ scale from reactor walls (boilers, heat exchangers), is treatment with caustic soda concentrated to about > 30% and at a temperature > 95° C, still according to the above reaction [1] read from right to left.

Also known per se is the possibility of obtaining aqueous solutions of alkaline phenates from sodium sulphate and sodium sulphite, lime and phenol in an aqueous solution at about 90°–100° C, under rather drastic conditions.

Thus, a principal object of this invention is that of providing an effective method, with fair industrial applicability, that will ensure the preparation of anhydrous organic solutions of alkaline phenates by reaction of alkaline sulphates, phenols and calcium hydroxide, with practically quantitative yields exceeding 97–98%.

This and still other objects of the invention are attained by a process for the preparation of anhydrous solutions of alkaline phenates in organic solvents comprising the following steps:

(1) synthesis in water medium of alkaline phenates by reaction of an alkaline sulphate selected from the class consisting of sodium sulphate and potassium sulphate, with calcium hydroxide and phenols of the general formula:

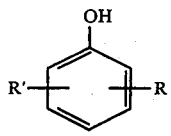

wherein R and R', which may be the same or different from each other, are hydrogen atoms or linear alkyl groups having from 1 to 4 carbon atoms, at temperatures substantially below 30° C and with molar ratios that are substantially stoichiometric;

(2) filtering the CaSO$_4$;

(3) quantitatively decalcifying the residual aqueous solution by the addition of an aqueous solution of an alkali selected from the class consisting of NaOH and KOH, until a total concentration is attained at least equal to about 30% by weight based on the total solution, and preferably between 30% and about 50%;

(4) filtering the Ca(OH)$_2$ and the alkaline sulphate precipitate;

(5) extracting in countercurrent, at a temperature between 50° and about 90° C, the residual aqueous solution with at least one aprotic polar organic solvent selected from the class consisting of cyclic ethers, polyethyleneglycol ethers, aromatic, heterocyclic and tertiary cycloaliphatic bases, sulphoxides, sulphones, possibly associated with a diluent which preferably is toluene; and at last (6) dehydrating by distillation the organic solution of the alkaline phenates thus obtained.

The main reactions involved in his procedure may be thus summarized:

for phase (1):

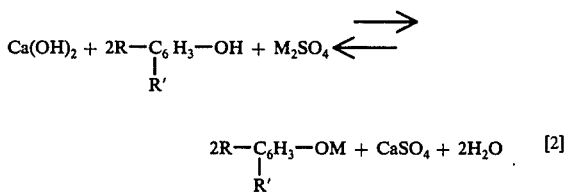

wherein R and R' have the meanings already given and wherein M is the alkaline metal; and for phase (3):

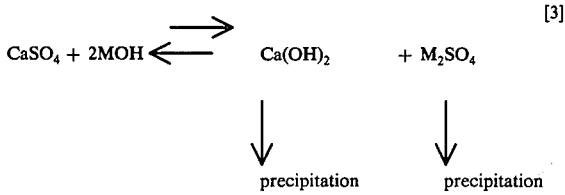

Generally speaking, then, the process which is the object of this invention consists or consists essentially in an effective combination of phases conducted within well-defined parametrical limits that insure an unforeseeable selectivity in the results and in high yields.

More particularly, when following the order of the phases indicated above, the synthesis of the alkaline phenate is carried out in water medium and the phenate is preferably a sodium or potassium phenate or cresolate.

Theoretically, alkaline phenates are in general compatible also with alkaline metals different from sodium or potassium which are of an easier and cheaper application and availability.

The reaction of phase (1) is carried out at a temperature below 30° C, thereby obtaining conversions of 97% and more. Reaction times around 1 hour are quite sufficient. After filtering (phase (2)), one proceeds, in phase (3), to the quantitative decalcification of the residual solution, as described, preferably at a temperature between about 40° and 60° C. The addition of the alkali may also occur in the solid state. Thereupon, after a second filtering (phase (4)), one proceeds to the step of extraction (phase (5)) with the described aprotic solvent.

Preferred solvents are: β-picoline, dimethylether of diethylene glycol (i.e., diglyme), quinoline, tetrahydrofuran, dimethyl sulphoxide, sulpholine, N-methyl-morpholine.

The aqueous solution coming from phase (3) has a concentration that lies, as indicated above, between 70% and about 50% in free alkali, expressed by weight on the total mass of the solution. In principle, besides the already indicated solvents, all the aprotic polar organic solvents are suitable which are stable in an alkaline medium, either miscible or immiscible in water and in which the phenates are soluble. Finally, in the extraction phase (5) there is an optional use of diluents selected from the class consisting of aliphatic, cycloaliphatic, aromatic hydrocarbons and/or their mixtures, having a boiling point between 80° and 130° C, but preferably toluene, in quantities of up to about 30% by weight. The diluent may facilitate the extraction by acting to assist in separating the two phases, i.e., the aqueous phase and the organic phase. In the residual aqueous phase, after the extraction with the organic solvent this latter is absent or present only in traces.

The concentration of the solutions of the phenates in the organic solvents thus obtained may vary, depending on the conditions, from 20% to about 30% by weight.

The process of this invention, according to one particularly effective form of the embodiment, may be carried out in the following way:

Into a suitable container, fitted with a stirring system, feeding device for the reactants, and a thermometer, are introduced the aqueous solution of the alkaline sulphate (Na$_2$SO$_4$ or K$_2$SO$_4$), phenol (e.g., ortho-cresol) and Ca(OH)$_2$, while maintaining the temperature at the desired value under constant stirring for about 1 hour. At the end the calcium sulphate thus formed as filtered and then washed with water.

To the residual aqueous solution, together with the wash water, is then added the aqueous, or even solid alkali (NaOH or KOH), at the desired temperature (about 60° C). The reaction mass is kept under stirring at the stabilized temperature. The precipitate thus obtained is then filtered and washed with water. To the combined aqueous solution and water is then added the organic solvent, and optionally the diluent, still under stirring and at the same temperature. Thereafter the two homogeneous phases, of which the organic phase contains the alkaline phenate, are separated. The dehydration of the organic extract is achieved by conventional distillation.

This invention, thanks to the high conversion yields and the purities of the solutions obtained, appears to be particularly advantageous and will now be described further in the following examples, which are given merely for illustrative purposes:

EXAMPLE 1

Into a three-necked glass flask of 1000 cc holding capacity, fitted with a stirrer, a dip thermometer, and provided with a dosing system for the reactants, there were introduced 71 g of $Na_2SO_4$ in 500 cc of $H_2O$ until fully dissolved. To this mixture were then added 108 g of o-cresol and 40 g of $Ca(OH)_2$ at 95% titre while maintaining the temperature at 25° C.

The mixture was allowed to react over a period of 1 hour under vigorous stirring. At the end of the reaction the calcium sulphate thus formed was filtered, and then washed with 5 portions of 100 cc each of water at 20° C.

Titration of the filtrate and of the washings with a solution of $H_2SO_4$ gave a total alkalinity corresponding to a conversion of the sodium sulphate to sodium o-cresolate of 98%.

The aqueous solution of the filtrate and of the washings was additioned at 60° C with 1000 g of solid NaOH in a glass reactor of 3000 cc holding capacity, kept under stirring and at a stabilized temperature. The precipitate thereby formed was then filtered and washed with water.

The filtrate and the washings from this latter operation were then added, in the reactor stabilized at 60° C, to 450 cc of β-picoline and 90 cc of toluene, under vigorous stirring.

On stopping the stirring, two homogeneous phases separated. The organic phase extract contained 126.7 g of sodium o-cresolate.

Upon dehydration of the above mentioned organic phase in a three-necked glass flask of 1000 cc, fitted with a dip-thermometer, a stirrer, and a rectifying filled-type column with separator and reflux coolant, there were separated by azeotropic distillation 90 cc of toluene and 24 cc of $H_2O$, while in the boiler there remained the anhydrous solution of 126.7 grams of sodium o-cresolate in 450 cc of β-picoline.

The total yield was greater than 97%.

EXAMPLE 2

Operating as in Example 1, but starting from 71 g of $Na_2SO_4$ in 500 cc of $H_2O$, and adding 94 g of phenol and 40 g of $Ca(OH)_2$ at a titre of 93.6%, and by maintaining the temperature at 25° C, the mixture was allowed to react for 30 minutes under vigorous stirring.

The gypsum that formed was filtered and washed with 5 portions (100 cc each) of water at 20° C. The conversion of the sodium sulphate to sodium phenate reached 99.2%.

Using in the successive phases the same quantities and the same operational procedures as described above in Example 1, at the end one obtains by azeotropic distillation a solution of 113.1 g of sodium phenate in 450 cc of β-picoline, and 90 cc of toluene and about 30 cc of $H_2O$.

EXAMPLE 3

Operating as in Example 2 but using as solvents those indicated in Table 1, there were obtained anhydrous sodium phenate solutions with the total yields as therein recorded.

TABLE 1

| Solvent | Total Yields |
| --- | --- |
| Quinoline | > 97% |

TABLE 1-continued

| Solvent | Total Yields |
| --- | --- |
| Dimethylether of diethylene gylcol | > 97% |
| Tetrahydrofuran (THF) | > 97% |
| Dimethyl sulphoxide (DMSO) | > 97% |
| Sulpholane | > 97% |
| N-methyl-morpholine | > 97% |

EXAMPLE 4

Into a three-necked, temperature stabilized glass reactor of 250 cc holding capacity, fitted with a stirrer, a dip-thermometer and a feeding system for the reactants, there were introduced 17.42 g of $K_2SO_4$ in 150 cc of $H_2O$ up to about complete solubilization, and thereafter 21.6 g of o-cresol and 8 g of $Ca(OH)_2$ at a 95% titre, while maintaining the temperature of 25° C. This mixture was then allowed to react for 1 hour under vigorous stirring. The filtered gypsum was then washed with 5 portions (30 cc each) of water at 20° C. The conversion of the potassium sulphate to potassium o-cresolate amounted to 97.5%.

The aqueous solution of the filtrate and of the washings was additioned at 60° C with 300 g of solid KOH in a 1500 cc glass reactor stabilized as to temperature. The precipitate that formed was then filtered and washed.

The filtrate and the washings from this latter operation were added under vigorous stirring, in the same 1500 cc reactor, temperature stabilized at 60° C, to 100 cc of β-picoline and 20 cc of toluene.

After stopping the stirring and separating the two phases, the organic phase, after dehydration in a three-necked 250 cc flask fitted with a dip-thermometer, a stirrer and a filled-type rectifying column with separator and reflux-coolant, contained 28.4 g of potassium of 20 cc of toluene and 12.22 cc $H_2O$.

Conversions of $K_2SO_4$ to potassium o-cresolate conducted under temperature conditions different from those described above gave the results summarized in the following Table 2.

TABLE 2

| Phenate | Temperature | Conversion of sulphate to phenate |
| --- | --- | --- |
| Potassium o-cresolate | 50° C | 86.0 % |
| Potassium o-cresolate | 25° C | 97.5 % |

From this table one will observe the lower conversion obtained at 50° C, given for purposes of comparison.

EXAMPLE 5

Operating as in Example 4, there were obtained anhydrous potassium o-cresolate solutions in other organic solvents as summarized below in Table 3:

TABLE 3

| Solvent | Total yields |
| --- | --- |
| Quinoline | > 97 % |
| Dimethylether of diethylene glycol | > 97 % |
| Tetrahydrofuran (THF) | > 97 % |
| Dimethyl sulphoxide (DMSO) | > 97 % |
| Sulpholane | > 97 % |
| N-methyl-morpholine | > 97 % |

EXAMPLES 6 (a – d)

Conversion operations of Na$_2$SO$_4$ to sodium phenate and sodium o-cresolate, under temperature conditions different from those already described, gave the results summarized below in Table 4:

TABLE 4

| Phenate | Temperature | Conversion of the sulphate to the corresponding phenate |
| --- | --- | --- |
| (a) Sodium phenate | 100° C | 86.3 % |
| (b) Sodium phenate | 25° C | 99.2 % |
| (c) Sodium o-cresolate | 25° C | 98.0 % |
| (d) Sodium o-cresolate | 80° C | 90.0 % |

Tests (a) and (d) are comparative tests conducted at temperatures higher than those according to the present process and yielding poorer results.

What is claimed is:

1. A process for the preparation of anhydrous solutions of alkaline phenates in organic solvents, comprising the steps:
  (a) synthesis in water of alkaline phenates by the reaction of an alkaline sulphate selected from the class consisting of sodium sulphate and potassium sulphate, with calcium hydroxide and a phenol of the general formula:

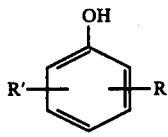

wherein R and R', which may be the same or different from each other, are hydrogen atoms or linear alkyl groups having from 1 to 4 carbon atoms, at a temperature substantially lower than 30° C;
  (b) filtering the calcium sulphate;
  (c) quantitatively decalcifying the residual aqueous solution, at a temperature between 40° and 60° C, by the addition of an aqueous solution of an alkali selected from the class consisting of NaOH and KOH, until a total concentration is reached which is between 30% and 50% by weight of the total solution;
  (d) filtering the precipitated calcium hydroxide and alkaline sulphate;
  (e) extracting in countercurrent, at a temperature between 50° and about 90° C, the residual aqueous solution with at least one aprotic polar organic solvent selected from the class consisting of $\beta$-picoline, dimethylether of diethylene glycol, quinoline, tetrahydrofuran, dimethylsulphoxide, sulpholane and N-methyl-morpholine; and
  (f) dehydrating the organic solution of the alkaline phenates.

2. A process according to claim 1, wherein the phenol is selected from the class consisting of phenol and the cresols.

3. A process according to claim 1, wherein the synthesis of the alkaline phenate is conducted according to substantially stoichiometric ratios between the reactants.

4. A process according to claim 1, wherein the organic solvent is combined with minor quantities of at least one diluent selected from the class consisting of aliphatic, cycloaliphatic and aromatic hydrocarbons having a boiling point between 80° and 130° C, in quantities up to about 30% by weight.

5. A process according to claim 4, wherein the diluent is toluene.

6. An anhydrous organic solution of an alkaline phenate obtained as described in claim 1.

* * * * *